(12) United States Patent
Koenig et al.

(10) Patent No.: US 7,235,263 B2
(45) Date of Patent: Jun. 26, 2007

(54) PROCESSES FOR CONTROLLING MICROBIAL ORGANIC COMPOUND PRODUCTION

(75) Inventors: David William Koenig, Menasha, WI (US); Bernard J. Minerath, Oshkosh, WI (US); Lindsay M. Gould, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 97 days.

(21) Appl. No.: 11/055,503

(22) Filed: Feb. 10, 2005

(65) Prior Publication Data

US 2005/0201968 A1    Sep. 15, 2005

Related U.S. Application Data

(62) Division of application No. 10/029,334, filed on Dec. 20, 2001, now Pat. No. 6,887,496.

(51) Int. Cl.
| | |
|---|---|
| *A61L 15/16* | (2006.01) |
| *A61L 15/20* | (2006.01) |
| *A61L 15/46* | (2006.01) |

(52) U.S. Cl. .................. 424/616; 424/65; 424/405; 424/409; 424/411; 424/414; 424/430; 424/431; 424/443; 424/445; 424/446; 514/23; 514/970

(58) Field of Classification Search ............... None
See application file for complete search history.

(56) References Cited

U.S. PATENT DOCUMENTS

| 959,605 A | 5/1910 | Queisser |
|---|---|---|
| 1,953,526 A | 4/1934 | Ainslie et al. |
| 2,430,450 A | 11/1947 | Brown et al. |
| 2,542,897 A | 2/1951 | Brown et al. |
| 2,542,898 A | 2/1951 | Brown et al. |
| 2,542,909 A | 2/1951 | De Wet |
| 3,406,015 A | 10/1968 | Foster et al. |
| 4,517,005 A | 5/1985 | Kolc et al. |
| 4,722,936 A | 2/1988 | Jacob |
| 4,722,937 A | 2/1988 | Jacob et al. |
| 4,863,445 A | 9/1989 | Mayhan et al. |
| 4,863,627 A | 9/1989 | Davies et al. |
| 5,110,593 A | 5/1992 | Benford |
| 5,182,373 A | 1/1993 | Kim et al. |
| 5,578,022 A | 11/1996 | Scherson et al. |
| 5,753,770 A * | 5/1998 | Breitenbach et al. .... 525/326.1 |
| 5,785,957 A * | 7/1998 | Losee et al. .................. 424/53 |
| 5,792,090 A | 8/1998 | Ladin |
| 5,855,570 A | 1/1999 | Scherson et al. |
| 6,000,403 A | 12/1999 | Cantwell |
| 6,025,186 A | 2/2000 | Kirk et al. |

FOREIGN PATENT DOCUMENTS

| DE | 3820726 A1 | 12/1989 |
|---|---|---|
| EP | 1 043 273 A1 | 10/2000 |
| GB | 1 267 618 | 3/1972 |
| GB | 2 023 430 A | 1/1980 |
| WO | WO 91/07184 | 5/1991 |
| WO | WO 99/08726 | 2/1999 |
| WO | WO 99/45973 | 9/1999 |
| WO | WO 99/45974 | 9/1999 |
| WO | WO 00/31145 | 6/2000 |
| WO | WO 01-49258 | 7/2001 |

OTHER PUBLICATIONS

The Merck Index (11th Ed. 1989), pp. 901,1375,1376.*
S. Tanatar, Double Compounds of Hydrogen Peroxide with Organic Substances, Journal of the Russian Physical Chemical Socienty, 1909, 40:376.
PCT/US02/22856 PCT International Search Report dated Oct. 30, 2002.

* cited by examiner

*Primary Examiner*—Johann Richter
*Assistant Examiner*—Frank I Choi
(74) *Attorney, Agent, or Firm*—Senniger Powers

(57) ABSTRACT

Processes for preparing products comprising an oxygen-generating additive for reducing the amount of skin irritation and inflamation and odor are disclosed. Specifically, products such as training pants and diapers are disclosed which contain a carbohydrate-hydrogen peroxide crystalline powder which, when wetted, produces a stream of oxygen which can be used by various bacteria on and near the wearer's skin during metabolism resulting in a significant decrease in the amount of volatile organic compounds produced by the bacteria during metabolism.

6 Claims, No Drawings

PROCESSES FOR CONTROLLING MICROBIAL ORGANIC COMPOUND PRODUCTION

REFERENCE TO RELATED APPLICATIONS

This divisional patent application claims priority from U.S. patent application Ser. No. 10/029,334 (U.S. Pat. No. 6,887,496 filed on Dec. 20, 2001, the entirety of which is hereby incorporated by reference.

BACKGROUND OF THE INVENTION

The present invention relates to products which reduce skin irritation, inflammation and odor by minimizing the production of volatile organic compounds by microbes at or near the skin's surface. More specifically, the present invention relates to products, such as diapers, incontinence garments, or training pants for example, which contain a stable carbohydrate-hydrogen peroxide mixture which, upon activation, releases a stream of oxygen which can act as a terminal electron (or hydrogen) acceptor during metabolism for bacteria on or near the skin's surface resulting in a significant decrease in the production of microbial produced volatile organic compounds. A preferred carbohydrate-hydrogen peroxide mixture is mannitol peroxide.

Human skin irritation and inflamation is typically the result of immunological events in the skin's surface that occur in response to exposure to skin irritants and/or skin injury. Inflamation and irritation is initiated by the production and release of pro-inflammatory mediators by skin cells which results in the recruitment and activation of circulating leukocytes. The process results in the hallmark features of skin irritation including redness, swelling and pain. It is well known that numerous molecules and microbes in aqueous and/or non-aqueous carriers on the skin can cause irritation resulting in skin inflammation.

Although little is known about the extent to which gas phase compounds, or metabolic gases, produced by microbes can initiate and/or exacerbate skin irritation and/or inflammation, it is believed that these gases can cause skin irritation and/or inflamation upon exposure. Gas phase molecules resulting from the activities of microorganisms are typically referred to as volatile organic compounds. Many volatile organic compounds produced by microbes at or near the skin's surface are well-known compounds such as oxalacetic acid, isovaleric acid, propionic acid, hexanoic acid, and the like, all of which are known skin irritants. While many of the volatile organic compounds produced by microorganisms are truly organic in nature as they contain carbon, some important compounds produced by microorganisms such as ammonia and hydrogen sulfide are inorganic. As used herein, the term "volatile organic compounds" is meant to include both the organic and inorganic metabolic gases and compounds produced by microbes at or near the skin's surface which may be irritating to the skin, and is also intended to include both organic and inorganic compounds produced by microbes which do not fully volatilize and which can remain on the skin surface or in solution, such as a urine solution.

The microbial flora of the skin, mucus membranes, and of bodily waste products such as feces, urine, menses, and nasal secretions are a major source of various types of bacteria which can produce significant amounts of volatile organic compounds. For example, facultative anaerobic bacteria present on and near the skin produce volatile organic compounds during metabolism when a sufficient amount of oxygen to act as a terminal electron (or hydrogen) acceptor is not present in the environment. Because human excrement contains such a large number of bacteria which can lay next to the skin after release, these volatile organic compounds may be a major unrecognized source of irritants to the skin, and therefore may be a major unrecognized element of skin irritation in the diapered, vaginal, wound, and nasal environments. Also, these volatile organic compounds may be a significant source of objectionable odors.

As such, a need exists in the infant care, adult care, wound management, and feminine care products industries for products which are capable of controlling and reducing the production of volatile organic compounds from microbes at or near the skin surface. Such a reduction in volatile organic compounds may result in a significantly reduced amount of skin irritation and inflamation on the skin of the wearer, and may also reduce the production of objectionable odors at or near the skin's surface.

SUMMARY OF THE INVENTION

The present invention provides products such as diapers, training pants, adult incontinence garments, tampons, interlabial pads, sanitary napkins, facial tissue and bath tissue, and wound management products which contain a stable oxygen producing compound which may be activated after insult to produce a stream of oxygen. The oxygen stream produced by the compound contained on or in the product can act as a terminal electron (or hydrogen) acceptor in the metabolism process of microbes on or near the skin's surface resulting in a significant decrease in the production of volatile organic compounds by these microbes. Such a decrease in volatile organic compound products leads to a reduced amount of skin irritation and inflammation, and may also result in the reduction in the production of offensive odors.

The oxygen producing compounds for incorporation into the products of the present invention are comprised of a carbohydrate-hydrogen peroxide mixture which has been crystallized into a stable crystalline material. Preferably, the oxygen producing compound is a crystalline compound comprised of a sugar alcohol-hydrogen peroxide mixture. A particularly preferred oxygen producing compound for incorporation into the products of the present invention is mannitol-peroxide.

Briefly, therefore, the present invention is directed to a product comprising a carbohydrate-hydrogen peroxide mixture for reducing the amount of irritation on a wearer's skin caused by microbial-produced volatile organic compounds. The mixture is capable of generating oxygen upon activation, and the oxygen acts as a terminal electron acceptor for bacteria on or near the skin's surface such that the production of volatile organic compounds by the bacteria is reduced.

The invention is further directed to a product comprising a sugar alcohol-hydrogen peroxide mixture for reducing the amount of irritation on a wearer's skin caused by microbial-produced volatile organic compounds. The mixture is capable of generating oxygen upon activation, and the oxygen acts as a terminal electron acceptor for bacteria on or near the skin's surface such that the production of volatile organic compounds by the bacteria is reduced.

The invention is further directed to a product comprising from about 0.01% (by weight of the product) to about 5% (by weight of the product) of a mannitol-hydrogen peroxide mixture for reducing the amount of irritation on a wearer's skin caused by microbial-produced volatile organic compounds. The mixture is capable of generating oxygen upon activation, and the generated oxygen acts as a terminal electron acceptor for bacteria on or near the skin's surface such that the production of volatile organic compounds by the bacteria is reduced.

The invention is further directed to a product comprising from about 0.01% (by weight of the product) to about 5% (by weight of the product) of a sorbitol-hydrogen peroxide mixture for reducing the amount of irritation on a wearer's skin caused by microbial-produced volatile organic compounds. The mixture is capable of generating oxygen upon activation, and the generated oxygen acts as a terminal electron acceptor for bacteria on or near the skin's surface such that the production of volatile organic compounds by the bacteria is reduced.

The invention is further directed to a process for preparing a product comprising a carbohydrate-hydrogen peroxide mixture for reducing the amount of irritation on a wearer's skin caused by microbial-produced volatile organic compounds. The mixture is capable of generating oxygen upon activation such that the oxygen acts as a terminal electron acceptor for bacteria on or near the skin's surface such that the production of volatile organic compounds by the bacteria is reduced. The process comprises first mixing a carbohydrate and hydrogen peroxide together to form a carbohydrate-hydrogen peroxide mixture and then heating the mixture at a temperature of at least about 90° C. for at least about 4.5 hours to evaporate off any solvent in the mixture and produce solid particles. Finally, the solid particles produced are incorporated into the product.

The invention is further directed to a process for preparing a product comprising a carbohydrate-hydrogen peroxide mixture for reducing the amount of irritation on a wearer's skin caused by microbial-produced volatile organic compounds. The mixture is capable of generating oxygen upon activation such that the oxygen acts as a terminal electron acceptor for bacteria on or near the skin's surface such that the production of volatile organic compounds by the bacteria is reduced. The process comprises first mixing a sugar alcohol and hydrogen peroxide together to form a sugar alcohol-hydrogen peroxide mixture and then heating the mixture at a temperature of at least about 97° C. for at least about 7 hours to evaporate off any solvent in the mixture and produce solid particles. Finally, the solid particles produced are incorporated into the product. Other objects and features of this invention will be in part apparent and in part pointed out hereinafter.

DETAILED DESCRIPTION OF THE PREFERRED EMBODIMENTS

In accordance with the present invention, it has been discovered that the production of volatile organic compounds by microbes on or near the skin's surface which may lead to skin irritation, inflamation, and infection, along with offensive odors, can be significantly reduced by introducing an oxygen producing compound into a product worn next to the skin that can be activated upon wetting. Because waste products produced by the human body such as feces are major sources for microbes which produce volatile organic compounds in the absence of sufficient oxygen for metabolism, the incorporation of the oxygen producing compound into products such as diapers, training pants and adult incontinence garments results in improved skin health as the microbes contained in these waste products, along with those naturally occurring on the skin, do not produce high amounts of volatile organic compounds in the presence of oxygen. Surprisingly, a stable carbohydrate-hydrogen peroxide compound can be incorporated into the products of the present invention such that when an insult occurs, a steady stream of oxygen is produced by the mixture in the product resulting in improved skin health and a reduced level of offensive odors. In a preferred embodiment, the carbohydrate-hydrogen peroxide compound comprises a sugar alcohol and hydrogen peroxide such as mannitol peroxide.

In accordance with the present invention, a carbohydrate-hydrogen peroxide mixture is introduced into or onto a product to minimize or substantially eliminate the production of volatile organic compounds by microbial metabolism. The microbes may be contained on or near the skin and in human waste products such as feces, urine, menses, and nasal secretions. The carbohydrate-hydrogen peroxide mixtures can be incorporated into or onto numerous products in accordance with the present invention such as, for example, diapers, training pants, adult incontinence garments, feminine napkins, paper towels, tampons, interlabial pads, facial tissue, wound management products, bath tissue, deodorant powder, deodorant sticks, diaper pails, liners for diaper pails, refuse containers, bed pads, puppy pads and other pet supply products. When these products, which contain the carbohydrate-hydrogen peroxide mixture, are insulted by urine or another liquid, the mixture releases a stream of oxygen into the product and onto the surrounding skin. This released oxygen can then participate in the metabolism of the bacteria present in and around the skin and exudate and act as an electron (or hydrogen) acceptor such that metabolism can occur in the presence of oxygen. With sufficient oxygen present, the production of volatile organic compounds by the bacteria is significantly minimized such that skin irritation, inflamation, and infection, along with offensive odors, caused by the volatile organic compounds are diminished.

The products of the present invention incorporating a carbohydrate-hydrogen peroxide mixture are highly useful in reducing the amount of volatile organic compounds produced by numerous types of bacteria. Specifically, the products of the present invention incorporating the carbohydrate-hydrogen peroxide mixture are particularly effective in reducing the amount of volatile organic compounds produced from facultative bacteria. Examples of facultative bacteria which can produce volatile organic compounds at or near the skin's surface include, but are not limited to, for example, *Escherichia, Klebsiella, Enterobacter, Serratia, Citrobacter, Corynebacterium, Propionibacterium, Neisseria, Pseudomonas, Vibrios, Shigellae, Salmonella, Proteus*, and *Moraxella*. A wide range of simple and complex carbohydrates can be combined with hydrogen peroxide to produce a compound that when insulted produces a stream of oxygen which can be utilized as an electron (or hydrogen) acceptor during metabolism by microbes on and near the skin surface. In a preferred embodiment of the present invention, the carbohydrate component of the carbohydrate-hydrogen peroxide compound or mixture is comprised of a sugar alcohol; that is the carbohydrate is comprised of an alcohol which has been derived from a sugar. One example of this is the derivitization of mannitol from sucrose. Such sugar alcohols may also be commonly referred to as polyols. Preferred sugar alcohols for use in combination with hydrogen peroxide to produce a carbohydrate-hydrogen peroxide mixture include dulcitol, arabitol, adonitol, mannitol, sorbitol, xylitol, lactitol, maltitol, dithioerythritol, dithiothreitol, glycerol, galactitol, erythritol, inositol, ribitol, and hydrogenated starch hydrolysates. Highly preferred sugar alcohols for use with hydrogen peroxide to produce a stable carbohydrate-hydrogen peroxide compound include mannitol and sorbitol.

In accordance with the present invention, the carbohydrate-hydrogen peroxide mixture may be prepared by mixing a carbohydrate, such as a sugar alcohol, together with the hydrogen peroxide and heating the mixture at a suitable temperature to drive off the solvent for a period of time of at least about 3 hours, more preferably at least about 4.5 hours, and still more preferably at least about 7 hours. After the solvent is removed, a crystalline powder is recovered. It is preferable that the heating be sufficient to drive off solvent, but not enough to boil the solvent. Heating temperatures sufficient to drive off the solvent in a timely manner are typically at least about 80° C., and preferably at least about 90° C. A particularly suitable temperature is about 97° C. Although a specific procedure for producing mannitol peroxide for use in the present invention is set forth below in the Examples, one specific method of producing carbohydrate-hydrogen peroxide crystals for incorporation into various products in accordance with the present invention is as follows: 1.5 parts (by weight) of 30% hydrogen peroxide is mixed together with 1 part (by weight) mannitol in a flask and heated to a temperature of from about 90° C. to about 100° C. for a period of about 7 hours. Enough heat is applied to evaporate solvent from the mixture, but not enough to boil the mixture. After heating is discontinued, any remaining solvent can evaporated by, for example, a vacuum, to produce a white crystalline powder comprising the mannitol-hydrogen peroxide mixture. Under typical circumstances, no solvent will remain after the 7 hour period. Another method of producing mannitol peroxide can be found in *Double Compounds of Hydrogen Peroxide With Organic Substances*, Tanatar, S. 1909, *Journal of the Russian Physical Chemical Society*, 40: pg. 376, the entirety of which is incorporated by reference.

A preferred method of preparing the carbohydrate-hydrogen peroxide mixtures for incorporation into the product of the present invention includes mixing 1.5 parts (by weight) of 30% hydrogen peroxide with 1 part (by weight) mannitol (or other carbohydrate) in a flask and heating the mixture to a temperature of about 97° C. for a period of at least about 4.5 hours, more preferably at least about 7 hours to evaporate the solvent and produce solid crystals. Typically, after heating the mannitol-hydrogen peroxide mixture for about 3 hours at 97° C., the solvent has completely evaporated and a white powder or crystalline material remains. In accordance with the present invention, it is preferred that the powderous or crystalline material recovered after evaporation (i.e., the carbohydrate-hydrogen peroxide mixture) be allowed to remain in the oven (or other drying or heating apparatus) at the drying or heating temperature for several more hours prior to use; that is, it is preferable that, including the time the solvent is being evaporated off of the carbohydrate-hydrogen peroxide mixture, the mixture remain in the oven at the drying temperature for a period of at least about 4.5 hours, and more preferably at least about 7 to 24 hours or longer prior to utilizing the mannitol peroxide in accordance with the present invention. Such an extended heating time of at least about 4.5 hours including the solvent evaporation significantly improves the resulting product's performance in the present invention in that the mixture does not significantly inhibit the growth of, or kill, the microbes.

Without being bound to a particular theory, it appears that, at heating temperatures less than about 100° C., if the carbohydrate-hydrogen peroxide mixture is not heated for a total period greater than about 4.5 hours (including the evaporation period), the mixture, when activated in a product of the present invention, is prone to releasing some highly reactive reaction products including reactive oxygen radicals and other radicals which can kill some or all of the bacteria, including naturally occurring bacteria, which may be beneficial or necessary for some purposes, in the area surrounding the release. It appears that when the mixtures are heated for a period of greater than about 4.5 hours, preferably greater than about 7 hours (including the evaporation time), a reduced amount of reactive radicals is released and the carbohydrate such as mannitol, for example, can act as a sufficient radical scavenger to reduce the available radicals such that released oxygen can be utilized by the bacteria in metabolism to minimize or eliminate volatile organic compound production. Such an effect is significant in that there is an advantage in simply minimizing or eliminating the metabolic compounds produced by bacteria and in not limiting the growth of or killing the bacteria present on and near the skin, mucosa, or within the body (i.e., if the products of the present invention are tampons). The killing of bacteria is typically non-selective; that is all bacteria are killed whether the bacteria are beneficial or non-beneficial. In the event of vaginal bacteria, for example, the killing of all bacteria in a specific area can be a serious problem as numerous bacterial species are required to maintain a healthy vaginal environment and balance the pH of the vagina. With the compounds and products of the present invention, only a very small amount, if any, bacteria is actually killed as the compounds simply supply oxygen for use during metabolism which reduces the production of the unwanted metabolic byproducts.

Without being bound to a particular theory, it is believed that the carbohydrate and the hydrogen peroxide do not chemically react with each other to form a new, different chemical substance, but rather simply complex together, possibly through hydrogen bonding, to form an intimate complexed mixture which maintains individual carbohydrate and individual hydrogen peroxide molecules. As such, the resulting crystals are comprised of both the carbohydrate and the hydrogen peroxide. Further, it is believed that when the carbohydrate-hydrogen peroxide crystals are introduced into a product such as a diaper, for example, and insulted, the moisture from the insult decomposes the crystals and releases the hydrogen peroxide, which begins to decompose into peroxide radicals and oxygen radicals. During this decomposition, it is believed that the carbohydrate (mannitol, for example) acts as a reducing agent and radical scavenger and reduces the oxygen and peroxide free radicals present in the mixture. From the decomposition of the hydrogen peroxide, in combination with the reducing agent which eliminates the oxidative compounds, water and oxygen is produced. It is the oxygen produced by the decomposition of the hydrogen peroxide which is believed to participate in the metabolism of the microbes decreasing the production of the volatile organic compounds.

In accordance with the present invention, the carbohydrate-hydrogen peroxide mixture is introduced into or onto the products of the present invention in an amount sufficient to produce a stream of oxygen upon insult such that metabolism of microbes on and near the surface of the skin or other surface can proceed with minimal production of volatile organic compounds. In typical embodiments, from about 0.01% (by weight of the substrate) to about 5% (by weight of the substrate), preferably from about 0.1% (by weight of the substrate) to about 1% (by weight of the substrate), preferably from about 0.1% (by weight of the substrate) to about 0.5% (by weight of the substrate) of the carbohydrate-hydrogen peroxide mixture is sufficient to provide the intended benefit. As used herein, the term "by weight of the substrate" means the total weight of the dry substrate before any addition of the carbohydrate-hydrogen peroxide mixture.

A significant and unexpected aspect of the products of the present invention which contain the carbohydrate-hydrogen peroxide mixtures is that the products have a particularly long shelf life; that is, the carbohydrate-hydrogen peroxide mixtures maintain the ability to produce a significant stream of oxygen and do not significantly decompose over extended periods of time. Although the carbohydrate-hydrogen peroxide compounds of the present invention may decompose slightly over extended periods of time, the compounds described herein are sufficiently stable such that even after extended periods of storage, a significant amount of oxygen can be produced upon activation. Specifically, carbohydrate-hydrogen peroxide mixtures have been found to maintain the ability to produce oxygen when wetted resulting in a decreased production of ammonia from bacteria when the carbohydrate-hydrogen peroxide mixtures were 3 months, 6 months, and even 12 months old. This indicates that the carbohydrate-hydrogen peroxide mixtures incorporated into the products of the present invention are highly stable oxygen producing products which, unless exposed to high humidity or liquids during storage, are stable for extended periods of time.

Another surprising and unexpected aspect of the products of the present invention is their ability to produce a steady, consistent stream of oxygen over an extended period of time after activation. Even after extended periods of storage as described above, the products of the present invention can produce a steady stream of oxygen for an extended period of time to decrease the production of metabolic products as described herein. This is a significant advantage in that in certain products, bacteria laden waste products may remain on or near the skin's surface for an extended period of time prior to removal allowing significant time for the production of metabolic products. Because the products of the present invention are capable of production a consistent stream of oxygen for an extended period of time after activation, the products are highly useful in significantly minimizing the production of metabolic compounds which can lead to skin irritation and foul odors.

The carbohydrate-hydrogen peroxide mixtures of the present invention may be introduced directly into or onto a product, or may first be encapsulated into a shell material which releases the carbohydrate-hydrogen peroxide mixture when wetted during use. The microencapsulated shell is constructed of a material such that it will release the carbohydrate-hydrogen peroxide crystals upon wetting. The shell may, optionally, have a coating thereon comprising a ligand which can selectively bind the shell containing the carbohydrate-hydrogen peroxide mixtures to living microbes. Such a ligand coating on the outside surface of the shell may improve the effectiveness of the carbohydrate-hydrogen peroxide mixtures described herein by targeting microbes for delivery of the mixtures upon urination.

The wetting of the microencapsulated shell may cause the shell material to solubilize, disperse, swell, disintegrate, or may be permeable such that it disintegrates or discharges the carbohydrate-hydrogen peroxide crystals upon wetting. Suitable microencapsulation shell materials include cellulose-based polymeric materials (e.g., ethyl cellulose), gelatin, carbohydrate-based materials (e.g., starches and sugars) and materials derived therefrom (e.g., dextrins and cyclodextrins) as well as other materials compatible with human tissues. The microencapsulation shell thickness may vary depending upon application, and is generally manufactured to allow the encapsulated crystals to be covered by a thin layer of encapsulation material, which may be a monolayer or thicker laminate layer, or may be a composite layer. The microencapsulation layer should be thick enough to resist cracking or breaking of the shell during handling or shipping of the product or during wear which would result in breakage of the encapsulation material and a premature release of the crystals. The microencapsulation layer should also be constructed such that humidity from atmospheric conditions during storage, shipment, or wear will resist a breakdown of the microencapsulation layer that would result in a premature release of the crystals.

Microencapsulated carbohydrate-hydrogen peroxide crystals should be located or be of a size such that the wearer cannot feel the encapsulated shell against the skin. Typically, the size of the microencapsulated shell should be no greater than about 25 micrometers. Although larger microencapsulated shell sizes may be utilized, they may result in a "gritty" or "scratchy" feeling on the skin of the wearer of the product.

The carbohydrate-hydrogen peroxide mixtures of the present invention may be incorporated directly into numerous products to control the production of volatile organic compounds from microbes present in human waste products and on or near the skin's surface. Specifically, the carbohydrate-hydrogen peroxide mixtures can be incorporated into cellulosic materials, non-woven materials, and superabsorbent materials such that, upon insult, a steady stream of oxygen is generated from the carbohydrate-hydrogen peroxide mixture.

Typically, the carbohydrate-hydrogen peroxide mixture is not simply introduced onto or into a product without a stabilizing mechanism to ensure that the crystals remain in the desired area of the product. The carbohydrate-hydrogen peroxide crystals can be introduced onto a product utilizing various methods including, for example, spray coating, slot coating, and printing, particle impingement, or a combination thereof. In spray coating, the carbohydrate-hydrogen peroxide mixture is thoroughly mixed with a substantially urine-soluble or urine-dispersable adhesive agent to disperse the carbohydrate-hydrogen peroxide crystals throughout the adhesive material. The adhesive material can comprise a urine-soluble adhesive which will partially or completely dissolve upon wetting with urine or other liquids and allow release of the carbohydrate-hydrogen peroxide mixture, or may be comprised of a material which disperses upon contact with urine allowing release of the mixture. Suitable adhesives include, for example, polyvinyl pyrrolidone and poylvinyl alcohol, and combinations thereof. After the adhesive and carbohydrate-hydrogen peroxide crystals are mixed, they can be applied by, for example, spraying, knifing, or roller coating, onto the desired area of the product and allowed to dry prior to packaging. It will be recognized by one skilled in the art that the crystals described herein can be distributed throughout the entire product, or can simply be introduced onto a particular area of a product depending upon the intended use of the product.

Similar to spray coating, the carbohydrate-hydrogen peroxide crystals may be introduced into or onto the products of the present invention through slot coating. In slot coating, an adhesive-carbohydrate-hydrogen peroxide mixture as described above is introduced directly onto the desired area of the pad in "slots," discrete row patterns, or other patterns. Upon wetting, the adhesive allows a release of the carbohydrate-hydrogen peroxide crystals. Slot coating may be advantageous in certain applications wherein it is not desirable to coat the entire surface with an adhesive. In some circumstances, an adhesive coating over an entire surface may retard quick absorption of urine or other exudates into an absorbent core. When slot coating is utilized, channels are created where no adhesive is present and exudates may drain quickly. Slot coating may also be advantageous in certain applications where precise control of the location of the carbohydrate-hydrogen peroxide crystals is desired. Generally, slot coating rows are evenly spaced across the surface upon which they are applied, but may be spaced in specific patterns with varying spacing if desired.

In an alternative embodiment, the carbohydrate-hydrogen peroxide mixture can also be introduced onto or into a gas permeable liner, absorbent core, or another layer of a product in accordance with the present invention through the use of a vacuum driving force or through the use of a pressure differential. When utilizing a vacuum force, the carbohydrate-hydrogen peroxide crystals are positioned on the liner, absorbent core, or another layer while a vacuum driving force is applied to the opposite side of the liner, absorbent core, or another layer to drive the crystals into the fabric matrix of the liner, core or other layer. Varying degrees of vacuum can be applied depending upon the required depth of the crystals. In this embodiment, no adhesive is required. Once in the fabric matrix of the product, the crystals are stable until wetted. Alternatively, electrostatic forces or other means may be utilized to stabilize the crystals on the surface of the product.

In an alternative embodiment of the present invention, the carbohydrate-hydrogen peroxide crystals can be incorporated in various products in accordance with the present invention by incorporating the crystals into a liposome carrier or emulsion and introducing the liposome carrier or emulsion into or onto the product in the desired amount. This type of delivery system for the carbohydrate-hydrogen peroxide crystals allows for incorporation of the active material into fibers as well as non-woven materials such as tissues, and into the solutions used in combination with wet wipes. Liposome carrier or emulsion systems may also be useable to incorporate the carbohydrate-hydrogen peroxide crystals into other products such as wound management products, feminine care products, bath tissue, adult incontinence garments, and/or deodorants.

The present invention is illustrated by the following examples which are merely for the purpose of illustration and is not to be regarded as limiting the scope of the invention or manner in which it may be practiced.

EXAMPLE 1

In this Example, *Proteus mirabilis* bacteria was grown under various growth conditions and analyzed to determine whether aeration of the bacteria during growth affected the production of compounds by the bacteria during growth that elicit an inflammatory response in human skin tissues.

1. Bacterial Preparation

*Proteus mirabilis* (ATCC 29906) were recovered from frozen state by growing the appropriate bacterial coated MicroBank Bead (Pro Lab, Austin Tex.) in 10 mL trypticase soy broth (TSB, Difco, Ann Arbor, Mich.) in a 15 mL sterile loosely tightened screw capped conical tube overnight at 37° C. The tube was held stationary. (*E. coli* (ATCC 8739), utilized in Example 6 herein, was recovered using the same procedure described herein for *Proteus mirabilis*). Upon observation of turbidity, the bacterial suspension was checked for purity by isolation plate and Gram stain. Once determined that the isolate was *Proteus mirabilis* (or *E. coli* in Example 6), a colony from the isolation plate was transferred to 10 mL of TSB in a 15 mL sterile screw capped conical tube and incubated overnight at 37° C. under facultative conditions. Samples of bacterial suspension resulting from this overnight TSB culture were used to initiate all experiments utilizing *Proteus mirabilis* bacteria (or *E. coli* in Example 6).

2. Growth of Bacteria in Urine for Production and Control of Skin Irritants

*Proteus mirabilis* was taken from a TSB culture (described in (1) above) and grown under various conditions for use in the Examples. For bacteria to be grown under aerobic conditions, 50 microliters of *Proteus mirabilis* was taken from a TSB culture prepared as described above and inoculated into a 50 mL volume of a freshly made 9:1 (by volume) pooled adult female urine:TSB mixture into a 250 mL shake flask. This mixture was rotated at 250 rpm at 37° C. overnight to grow the bacteria. For bacteria to be grown under facultative conditions, 10 microliters of *Proteus mirabilis* was taken from a TSB culture prepared as described above and inoculated into a 10 mL volume of a freshly made 9:1 (by volume) pooled adult female urine:TSB mixture into a 15 mL tube. The tube was loosely fitted with a screw cap, and held stationary at 37° C. overnight to grow the bacteria. For bacteria to be grown under anaerobic conditions, 10 microliters of *Proteus mirabilis* was taken from a TSB culture prepared as described above and inoculated into a 10 mL volume of a freshly made 9:1 (by volume) pooled adult female urine:TSB mixture into a 15 mL conical tube. The tube was purged with nitrogen and a screw cap tightly closed, and then was held stationary overnight at 37° C. to grow the bacteria.

3. Test Method for Analysis of Skin Insult

In order to evaluate the amount of skin irritation by various samples prepared in the Examples, a human skin culture was selected to model the response of the human epidermis to treated and untreated bacterial metabolized urine:TSB mixture. The tissue model selected was an EPIOCULAR Tissue Model (OCL-200 propagated without hydrocortisone), and was purchased from MatTek Corporation (Ashland, Mass.). This model consists of normal, human-derived epidermal keratinocytes, which have been cultured to form a stratified, squamous epithelium similar to that found in the cornea. The epidermal cells, which are cultured on specially prepared cell culture inserts using a serum free medium, differentiate to form a multi-layered structures which closely parallel the corneal epithelium. Experiments using this skin culture were conducted in six parallel wells. Each well contained one milliliter of prewarmed media that was the same as the model skin culture media. The plates were then incubated in a 37° C., 5% carbon dioxide atmosphere for thirty minutes. After incubation, 25 microliters of the sample were applied to the surface of the model skin culture after removing any residual media.

After application of the test solution, the well plates were incubate for 6 hours in the 37° C., 5% carbon dioxide atmosphere. At the end of 6 hours, the well plates were removed from the incubator and the underlying media removed and stored at −80° C. The response of the skin culture to test the compositions/control and the insult solution is determined by measuring the amount of interleukin-1 alpha (IL-1a) and/or interleukin-8 (IL-8). IL-1a and IL-8 were quantified using an Interleukin-1 alpha or Interleukin-8 Quantikine Kit available from R&D Systems (Minneapolis, Minn.).

4. Viability of Skin Culture Test Method

To insure that the samples did not affect the viability of the skin culture, a MTT (3-[4,5-Dimethylthiazol-2-yl]-2,5-diphenyltetrazoliumbormide (Sigma Chemical Company, St. Louis, Mo.) assay was done. The reduction of the dye, which was taken up by the cells as a result of cellular metabolism, was used to measure the cytotoxicity of the test compositions. In order to confirm viability, inserts of the skin culture that had previously been subjected to the test composition insults were removed from their media and were washed consecutively through immersion in three different beakers of Phosphate Buffered Saline at a pH of 7.4. Fresh Phosphate Buffered Saline was used for each sample evaluated. The Phosphate Buffered Saline was discarded onto a paper towel, and the skin culture inserts were then patted onto the paper towel and placed into the wells of a 24 well plate containing 300 microliters of pre-warmed media. After all of the skin culture inserts were washed, they were transferred to new 24 well plates containing 300 microliters of the MTT reagent. The plates were incubated for 2 hours in a 37° C., 5% carbon dioxide atmosphere. After incubation, the skin culture inserts were transferred to 24 well plates and were immersed in 2 milliliters of MTT extraction buffer. The extraction buffer extracted the MTT reagent from the cells. The 24 well plates were parafilmed, covered and placed in airtight bags to reduce evaporation of the extraction buffer. The covered plates were rocked overnight in the dark and then the liquid in the skin culture inserts decanted back into the wells. The contents of each well were mixed and a 200 microliter aliquot was then removed from each well and transferred to a 96 well plate. The optical density of the samples was measured at 570 nanometers using a spectrophotometer (Molecular Devices, Sunnyvale, Calif.). The reading was subtracted from a background reading at 650 nanometers to improve data quality. Percent viability of each test composition relative to a PBS treated control was recorded as the Mean OD (test composition) divided by the Mean OD (PBS control) and the quotient then multiplied by 100.

In this Example, five samples were prepared and analyzed to determine: (1) Bacterial Yield (CFU/mL) calculated from optical density; (3) Percent viability of EPIOCULAR; and (4) EPIOCULAR IL-8. The samples included: (1) Deionized Water; (2) A urine:TSB mixture (9:1 by volume) as described above; (3) A urine:TSB mixture containing *Proteus mirabilis* bacteria grown under aerobic conditions as described above; (4) A urine:TSB mixture containing *Proteus mirabilis* bacteria grown under facultative conditions as described above; and (5) A urine:TSB mixture containing *Proteus mirabilis* bacteria grown under anaerobic conditions as described above. Table 1 sets forth the data collected for each sample.

TABLE 1

| Sample | Bacterial Yield (CFU/mL) | % Viability EPIOCULAR (n = 3) | EPIOCULAR IL-1a (pg/mL) (n = 3) |
|---|---|---|---|
| Deionized Water | N/A | 100 ± 19.5 | 22.78 ± 7.3 |
| Urine:TSB | N/A | 96.5 ± 9.2 | 22.14 ± 9.3 |
| Urine:TSB:Aerobic | 3.9E+9 | 81.3 ± 4.0 | 25.96 ± 4.1 |
| Urine:TSB:Facultative | 1.3E+9 | 58.7 ± 11.6 | 163.5 ± 49.37 |
| Urine:TSB:Anaerobic | 1.1E+9 | 75.6 ± 9.3 | 161.1 ± 49.37 |

As the data in Table 1 indicates, bacterial cell yields for all samples wherein *Proteus mirabilis* bacteria were introduced were similar. Also, the percent viability of the EPIOCULAR skin tissues remained fairly constant amongst the samples indicating that the skin cultures were alive after testing. The EPIOCULAR IL-1a produced for the deionized water, urine:TSB mixture and urine:TSB:aerobically cultivated bacteria was approximately equal, which indicated that the amount of insult on the EPIOCULAR skin culture was about the same for these samples. However, the IL-1a produced for the samples containing facultative and anaerobic cultivated bacteria was much higher compared to the first three samples. This increase in IL-1a for samples containing bacteria grown in oxygen deficient environments indicates that by increasing the aeration (i.e., oxygen during growth of the bacteria) the compounds made by the bacteria under various conditions change. Aeration appears to substantially reduce the compounds produced by bacteria that elicit an inflammatory response in EPIOCULAR skin cultures (IL-1a).

EXAMPLE 2

In this Example, *Proteus mirabilis* bacteria were grown under various conditions in a urine:TSB mixture and the samples analyzed to determine whether aeration of the bacteria during growth affected the production ammonia by the bacteria.

In this Example, five samples were prepared and analyzed. The first sample comprised deionized water. The second sample comprised a urine:TSB mixture as described in Example 1. The third sample comprised urine:TSB:aerobically grown bacteria, and was prepared as described in Example 1. The fourth sample comprised urine:TSB:facultatively grown bacteria, and was prepared as described in Example 1. The fifth sample comprised urine:TSB:anaerobically grown bacteria, and was prepared as described in Example 1.

Upon completion of the respective incubation periods of the samples, optical density measurements of each sample were taken as described above and ammonia production of the growth solutions was measured using an ammonia combination probe (Beckman, Fullerton, Calif.) by record mV using an Orion pH meter (Orion, Boston, Mass.). Orion ammonia standards (Orion) were used to calibrate the instrument.

Table 2 provides the data obtained in this Example 2, and shows bacterial CFU/milliliter for each sample, production of ammonia per sample (in ppm), and the amount of ammonia production per cell.

TABLE 2

| Sample | Bacterial Yields (CFU/mL) | Ammonia Production (ppm) | Ammonia/Cell (ppm/CFU × 10E+8) |
|---|---|---|---|
| Deionized Water | N/A | N/A | N/A |
| Urine:TSB | N/A | 17.68 | N/A |
| Urine:TSB:Aerobic | 3.9E+9 | 109.3 | 2.3 |
| Urine:TSB:Facultative | 1.3E+9 | 76.2 | 4.5 |
| Urine:TSB:Anaerobic | 1.1E+9 | 94.1 | 7.0 |

As the data in Table 2 indicates, for samples wherein *Proteus mirabilis* was introduced, aerobically grown bacteria produced the least amount of ammonia per bacterial cell followed by facultative and anaerobic bacteria. This indicates that by increasing the aeration (i.e., the amount of oxygen available during growth) during bacterial growth, the amount of ammonia production by the bacterial cells is decreased.

EXAMPLE 3

In this Example, mannitol peroxide was introduced into various samples and the samples analyzed to determine whether, under certain conditions, it could decrease the amount of ammonia production by bacteria in urine.

1. Mannitol Peroxide Production

Hydrogen Peroxide (22.5 mL of 30% hydrogen peroxide obtained from Sigma Chemical, St. Louis, Mo.) was mixed with mannitol (15 grams obtained from Sigma Chemical, St. Louis, Mo.) in a 300 mL Pyrex Fleaker. The mannitol was dissolved completely using heat and the Fleaker containing the mannitol-hydrogen peroxide solution was placed, without a cap, into a forced air oven (97° C.). The liquid was allowed to evaporate resulting in a dried white crystalline material observed after approximately three hours of drying. Multiple batches were made that had residence times in the oven of 3, 4.5, 7, and 24 hours. With the exception of Example 8 wherein mannitol peroxide having residence times of 3 hours, 4.5 hours, 7 hours, and 24 hours were tested, all Examples herein utilized mannitol peroxide having a residence time of 7 hours.

In this Example, six different samples were prepared for analysis. The first sample comprised a urine:TSB mixture that was prepared in the same manner as that described in Example 1. The second sample comprised a urine:TSB:5% mannitol peroxide mixture that was prepared in the same manner as sample 1, with the exception that 5% mannitol peroxide (w/v) was added to the mixture. The third sample comprised urine:TSB:10% mannitol peroxide, and was prepared similarly to sample 2 with the exception that 10% mannitol peroxide was added to the mixture. The fourth sample containing urine:TSB:facultatively grown *Proteus mirabilis* bacteria:5% mannitol peroxide (w/v) was prepared as follows: 50 microliters of *Proteus mirabilis* was taken from a TSB culture prepared as described above and inoculated into a 10 mL volume of a freshly made 9:1 (by volume) pooled adult female urine:TSB mixture into a 15 mL tube. The tube was loosely fitted with a screw cap, and held stationary at 37° C. overnight to grow the bacteria. An appropriate amount of mannitol peroxide was added to a fresh 10 mL volume of urine:TSB (9:1 by volume) in a 15 mL conical tube to produce a 5% (w/v) solution of mannitol peroxide. To this mixture of mannitol peroxide was added 10 microliters of the overnight urine:TSB grown bacteria, and this mixture was allowed to incubate at 37° C. overnight to grow the bacteria under facultative conditions. The fifth sample comprising urine:TSB:*Proteus mirabilis* (facultatively grown) was prepared in the same manner as that described in Example 1. The sixth sample comprising urine:TSB:facultative bacteria:10% mannitol peroxide was prepared the same as sample 4 with the exception that 10% mannitol peroxide was utilized.

The samples were analyzed for optical density and for ammonia content as described in Example 2 above. Table 3 shows the data collected for each sample.

TABLE 3

| Sample | Bacterial Yields (CFU/mL) | Ammonia Produced (ppm) (n = 3) | Ammonia/cell (ppm/CFU E+8) |
|---|---|---|---|
| Urine:TSB | N/A | 22.0 ± 5.7 | N/A |
| Urine:TSB:5% Mannitol Peroxide | N/A | 12.3 ± 0.5 | N/A |
| Urine:TSB:10% Mannitol Peroxide | N/A | 13.2 ± 0.9 | N/A |
| Urine:TSB:Facultative | 1.10E+9 | 69.9 ± 1.1 | 4.3 |
| Urine:TSB:Facultative:5% Mannitol Peroxide | 1.30E+9 | 34.5 ± 12.6 | 1.6 |
| Urine:TSB:Facultative:10% Mannitol Peroxide | 8.20E+8 | 13.9 ± 0.3 | 0.01 |

As shown in Table 3, the mannitol peroxide decreased ammonia production per bacterial cell in the samples containing *Proteus mirabilis* bacteria. As the amount of mannitol peroxide increased in the bacteria-containing sample from 5% to 10%, the amount of ammonia produced per cell dropped substantially. Without being bound to a particular theory, it appears that the mannitol peroxide crystals decompose in the presence of the urine and produce oxygen which is ultimately utilized by the bacteria during metabolism which results in the bacteria producing a reduced amount of ammonia, which is a known skin irritant.

EXAMPLE 4

In this Example, three separate samples were prepared and analyzed to measure the percent reduction of ammonia production in bacteria when differing amounts of mannitol peroxide were utilized.

The first sample comprised urine:TSB:facultatively grown *Proteus mirabilis* as prepared and described in Example 1. The second sample comprised urine:TSB:facultatively grown *Proteus mirabilis*:5% mannitol peroxide as prepared and described in Example 3. The third sample was prepared in the same manner as the second sample with the exception that 10% mannitol peroxide was incorporated into the mixture.

Each sample was analyzed for bacterial cell yield by optical density as described in Example 1, and was analyzed for ammonia content as described in Example 2. The data collected is shown in Table 4.

TABLE 4

| Sample | Bacterial Yields (CFU/mL) | Ammonia (ppm) (n = 3) | Ammonia/ Cell (ppm/CFU E+8) | % Reduction of Ammonia |
|---|---|---|---|---|
| Urine:TSB:Facultative | 1.10E+9 | 69.9 ± 1.1 | 4.3 | N/A |
| Urine:TSB:Facultative: 5% Mannitol Peroxide | 1.30E+9 | 34.5 ± 12.6 | 1.6 | 53.6 |
| Urine:TSB:Facultative: 10% Mannitol Peroxide | 8.2E+8 | 13.9 ± 0.3 | 0.01 | 98.5 |

The data in Table 4 shows that the mannitol peroxide had very little, if any, impact on the growth of the cells, but did significantly impact the production of ammonia by the bacteria. The mannitol peroxide significantly decreased the production of ammonia per cell. The effect of the mannitol peroxide appears to be dose dependent as the percentage decrease in ammonia production increased as the amount of mannitol peroxide increased.

EXAMPLE 5

In this Example four samples were prepared and analyzed to determine whether mannitol peroxide could reduce the production of compounds by bacteria that induce an IL-1a and a IL-8 response in EPIOCULAR skin cultures.

The first sample comprised urine:TSB and was prepared in the same manner as the urine:TSB sample in Example 1. The second sample comprised urine:TSB:facultatively grown Proteus mirabilis and was prepared in the same manner as the urine:TSB:facultative bacteria in Example 1. The third sample comprised urine:TSB:facultatively grown Proteus mirabilis:5% mannitol peroxide (w/v) and was prepared in the same manner as sample 3 in Example 3. The fourth sample comprised urine:TSB:facultatively grown Proteus mirabilis:10% mannitol peroxide (w/v) and was prepared in the same manner as sample 3 with the exception that it contained 10% mannitol peroxide (w/v).

After the incubation of each sample, bacterial CFU/milliliter and EPIOCULAR viability readings were obtained as set forth in Example 1. Also, each sample was used to challenge EPIOCULAR skin cultures as set forth in Example 1 to determine whether IL-1a and/or IL-8 was produced. The raw data collected is set forth in Table 5.

TABLE 5

| Sample | Bacterial Yields (CFU/mL) | % Viability EPIOCULAR | IL-1a (pg/mL) | IL-8 (pg/mL) |
|---|---|---|---|---|
| Urine:TSB | N/A | 93.04 ± 4.4 | 2.82 ± 0.38 | 9521.45 ± 1646.31 |
| Urine:TSB:Facultative | 1.10E+9 | 59.13 ± 8.2 | 124.91 ± 18.59 | 27423.23 ± 786.66 |
| Urine:TSB:Facultative:5% Mannitol Peroxide | 1.30E+9 | 78.26 ± 7.6 | 48.12 ± 8.93 | 27224.30 ± 2432.83 |
| Urine:TSB:Facultative:10% Mannitol Peroxide | 8.20E+8 | 77.39 ± 10.3 | 15.26 ± 12.80 | 15884.57 ± 839.53 |

As shown in Table 5, adding mannitol peroxide during growth of the bacteria impacts the compounds made by the bacteria which leads to a reduction in the amount of IL-1a produced by EPIOCULAR. Further, the amount of IL-8 produced by EPIOCULAR also decreased with increasing amounts of mannitol peroxide additions.

EXAMPLE 6

In this Example four samples were prepared and analyzed to determine whether mannitol peroxide could reduce the production of compounds by E. coli bacteria that induce an IL-8 and/or an IL-1a response in EPIOCULAR skin cultures.

The four samples were prepared identically to the four samples in Example 5 with the exception that facultatively grown E. coli was utilized as the bacteria in place of the Proteus mirabilis bacteria. The process for growing facultatively grown E. coli is set forth in Example 1.

After incubation, each sample was analyzed for EPIOCULAR viability and bacterial cell count as set forth in Example 1. Each sample was also used to challenge EPIOCULAR skin cultures to determine if IL-8 was produced. The raw data collected is set forth in Table 6.

TABLE 6

| Sample | Bacterial Yields (CFU/mL) | Ammonia (ppm) | % Viability (n = 3) | IL-8 (pg/mL) (n = 3) |
|---|---|---|---|---|
| Urine:TSB | N/A | 17.68 | 87.1 ± 5.4 | 920.91 ± 78.95 |
| Urine:TSB:Facultative | 5.86E+9 | 17.96 | 97.4 ± 0.6 | 1965.25 ± 53.68 |
| Urine:TSB:Facultative:5% MP | 2.14E+9 | 12.46 | 84.4 ± 2.8 | 1769.31 ± 103.9 |
| Urine:TSB:Facultative:10% MP | 4.98E+9 | 14.04 | 86.1 ± 3.3 | 1336.69 ± 60.84 |

Table 6 sets forth the data collected and shows that the addition of mannitol peroxide to the samples reduced the amount of IL-8 insult to the EPIOCULAR skin cultures.

EXAMPLE 7

In this Example, five samples were prepared to determine whether mannitol, in the absence of hydrogen peroxide, would reduce the amount of ammonia produced by Proteus mirabilis bacteria in a urine:TSB mixture.

The first sample comprised urine:TSB and was prepared in a similar manner to the urine:TSB sample in Example 1. The second sample comprised urine:TSB:facultatively grown Proteus mirabilis, and was prepared in a similar manner to the urine:TSB:facultative bacteria sample in Example 1. The third sample comprised urine:TSB:facultatively grown Proteus mirabilis:10% (w/v) mannitol and was prepared in a similar manner to sample number 3 in Example 3, with the exception the mannitol was substituted for the mannitol peroxide. The fourth sample comprised urine:TSB:10% mannitol and was prepared similarly to sample 1 with the exception that 10% mannitol (w/v) was added. The fifth sample comprised urine:TSB:facultatively grown Proteus mirabilis:5% mannitol peroxide and was prepared similarly to sample 3 with the exception that mannitol peroxide was used in place of mannitol.

After incubation, each sample was analyzed for ammonia content and bacterial cell yields. The raw data collected is shown in Table 8.

TABLE 7

| Sample | Bacterial Yields (CFU/mL) | Ammonia Produced (ppm) (n = 3) | Ammonia/Cell (ppm/10E8CFU) |
|---|---|---|---|
| Urine:TSB | N/A | 43.3 ± 1.2 | N/A |
| Urine:TSB:10% Mannitol | N/A | 42.6 ± 0.1 | N/A |
| Urine:TSB:Facultative | 7.53E+8 | 639.4 ± 1.8 | 79.2 |
| Urine:TSB:Facultative:10% Mannitol | 6.91E+8 | 621.6 ± 1.8 | 83.8 |

TABLE 7-continued

| Sample | Bacterial Yields (CFU/mL) | Ammonia Produced (ppm) (n = 3) | Ammonia/Cell (ppm/10E8CFU) |
|---|---|---|---|
| Urine:TSB:facultative: 5% Mannitol Peroxide | 8.93E+8 | 434.5 ± 7.5 | 43.84 |

As the raw data shows and FIG. 7 illustrates, mannitol in the absence of hydrogen peroxide does not significantly impact the production of ammonia in the bacteria.

EXAMPLE 8

In this Example, various concentrations of mannitol peroxide and mannitol were tested in the presence of aerobically cultivated *Proteus mirabilis*, urine and TSB to determine whether the mannitol peroxide or mannitol significantly impacted bacteria growth. The mannitol peroxide utilized in the samples of this Example were subjected to different drying procedures to determine whether length of drying of the mannitol peroxide had any effect on the growth of bacteria.

*Proteus mirabilis* was cultured in TSB as described in Example 1 and transferred to a urine:TSB mixture (9:1) and incubated under aerobic conditions as described in Example 1. A 10% solution (by weight) of each timepoint-batch of mannitol peroxide was prepared by mixing 1 gram of mannitol peroxide (or mannitol alone for some samples as indicated in Table 8 below) into 10 mL urine:TSB (9:1) mixture in a 15 mL screw top conical tube. The mixture was heated for about 30 minutes at about 37° C. to help solubilize the mannitol peroxide. In a 96-well microtiter plate with a lid, 150 microliters of each 10% solution was introduced into the first and second columns of the wells. Using a multi-channel pipette, 150 microliters of urine:TSB mixture was introduced into each well except the first column. Beginning at the second column of wells, serial dilutions were made by removing 150 microliters from the second column and transferring it to the third column. The mixture was mixed by pipetting up and down three times. The serial dilutions continued across each column of the plate and, after column 11, 150 microliters was discarded leaving column 12 as the 0% solution. Each well was then inoculated with 1 microliter of *Proteus mirabilis*, except for the negative control rows. One to three drops of anti-fogging solution was place on the plate lids with a cotton applicator, and allowed to air dry. The mixtures were incubated for 48 hours at 37° C. under aerobic conditions.

After incubation of the samples, each was analyzed for bacterial cell growth utilizing the optical density procedure as set forth in Example 1. The raw data for the optical density measurements is set forth in Table 8.

The data set forth in Table 8 indicates that the amount of time that the mannitol peroxide is heated during the drying step of the synthesis is an important factor in whether the mannitol peroxide ultimately inhibits the growth of bacteria. Mannitol alone appears to have no effect on cell growth at low concentrations, and appears to have little, if any, effect on cell growth at elevate concentrations. Similarly, mannitol peroxide that is subjected to heating for at least about 7 hours at a temperature of about 97° C. during the synthesis process also appears to have little effect on the growth of the bacteria, even at elevated concentrations. As discussed above, it is beneficial to incorporate oxygen producing compounds into the products of the present invention such that the compounds do not kill or inhibit the growth of a substantial amount of bacteria as some bacteria are required for maintaining good health.

In view of the above, it will be seen that the several objects of the invention are achieved. As various changes could be made in the above-described products without departing from the scope of the invention, it is intended that all matter contained in the above description be interpreted as illustrative and not in a limiting sense.

What is claimed is:

1. A process for preparing an absorbent product comprising a carbohydrate-hydrogen peroxide mixture for reducing the amount of irritation on a wearer's skin caused by microbial-produced volatile organic compounds, the mixture being capable of generating oxygen upon activation, the oxygen acting as a terminal electron acceptor for bacteria on or near the skin's surface such that the production of volatile organic compounds by the bacteria is reduced, the process comprising:
   mixing a carbohydrate and hydrogen peroxide together to form a carbohydrate-hydrogen peroxide mixture;
   heating the carbohydrate-hydrogen peroxide mixture at a temperature of at least about 90° C. for at least about 4.5 hours to evaporate off any solvent in the mixture and produce solid particles; and
   incorporating the solid particles into the absorbent product, wherein the absorbent product is selected from the group consisting of diapers, training pants, adult incontinence garments, feminine napkins, and interlabial pads.

2. The process as set forth in claim 1 wherein the mixture is heated for a period of at least about 7 hours prior to incorporation into the product.

3. The process as set forth in claim 1 wherein the mixture is heated for a period of at least about 24 hours prior to incorporation into the product.

4. The process as set forth in claim 1 wherein the carbohydrate is selected from the group consisting of dulcitol, arabitol, adonitol, mannitol, sorbitol, xylitol, lactitol,

TABLE 8

| Time in 97° C. Oven | 10% | 5% | 2.5% | 1.25% | 0.625% | 0.313% | 0.156% | 0.0785% | 0.0391% | 0.0195% | 0.0097% | 0% |
|---|---|---|---|---|---|---|---|---|---|---|---|---|
| 24 Hr. | 0.80 | 0.88 | 0.93 | 0.95 | 0.96 | 0.97 | 0.97 | 0.97 | 0.99 | 0.98 | 0.99 | 1.00 |
| 7 Hr. | 0.82 | 0.90 | 0.97 | 0.98 | 0.99 | 0.96 | 1.00 | 0.98 | 0.95 | 0.98 | 0.98 | 0.98 |
| 4.5 Hr. | 0.04 | 0.87 | 0.97 | 0.99 | 0.93 | 0.99 | 0.98 | 0.99 | 0.99 | 0.98 | 0.97 | 1.00 |
| 3 Hr. | 0.03 | 0.03 | 0.03 | 0.04 | 0.99 | 0.83 | 0.99 | 0.97 | 0.94 | 0.94 | 0.98 | 0.98 |
| Mannitol Alone | 0.87 | 0.89 | 0.99 | 1.02 | 0.98 | 0.92 | 0.92 | 0.97 | 0.97 | 0.98 | 0.98 | 1.00 | maltitol, dithioerythritol, dithiothreitol, glycerol, galactitol, erythritol, inositol, ribitol, hydrogenated starch hydrolysates, and mixtures and combinations thereof.

5. A process for preparing an absorbent product comprising a carbohydrate-hydrogen peroxide mixture for reducing the amount of irritation on a wearer's skin caused by microbial-produced volatile organic compounds, the mixture being capable of generating oxygen upon activation, the oxygen acting as a terminal electron acceptor for bacteria on or near the skin's surface such that the production of volatile organic compounds by the bacteria is reduced, the process comprising:

mixing a sugar alcohol and hydrogen peroxide together to form a sugar-alcohol-hydrogen peroxide mixture;

heating the sugar alcohol-hydrogen peroxide mixture at a temperature of at least about 97° C. for at least about 7 hours to evaporate off any solvent in the mixture and produce solid particles; and incorporating the solid particles into the absorbent product, wherein the absorbent product is selected from the group consisting of diapers, training pants, adult incontinence garments, feminine napkins, and interlabial pads.

6. The process as set forth in claim 5 wherein the sugar alcohol is selected from the group consisting of mannitol and sorbitol.

* * * * *